(12) United States Patent
Onoyama et al.

(10) Patent No.: US 7,065,238 B2
(45) Date of Patent: Jun. 20, 2006

(54) DEFECT INSPECTION METHOD AND DEFECT INSPECTION EQUIPMENT

(75) Inventors: Ayumu Onoyama, Tokyo (JP); Koichi Sakurai, Tokyo (JP); Kazuhiro Oka, Tokyo (JP); Hiroyuki Ishii, Tokyo (JP); Katsuhiro Fujiyoshi, Tokyo (JP)

(73) Assignee: Mitsubishi Denki Kabushiki Kaisha, Tokyo (JP)

( * ) Notice: Subject to any disclaimer, the term of this patent is extended or adjusted under 35 U.S.C. 154(b) by 583 days.

(21) Appl. No.: 09/948,045

(22) Filed: Sep. 7, 2001

(65) Prior Publication Data

US 2003/0048940 A1 Mar. 13, 2003

(51) Int. Cl.
*G06K 9/00* (2006.01)
*H04N 7/18* (2006.01)

(52) U.S. Cl. .................. 382/141; 382/274; 348/86; 348/125; 438/16

(58) Field of Classification Search ........ 382/141–152, 382/274; 348/86–95, 125–134; 700/110, 700/95; 438/16
See application file for complete search history.

(56) References Cited

U.S. PATENT DOCUMENTS 5,454,049 A * 9/1995 Oki et al. ................. 382/172

(Continued)

FOREIGN PATENT DOCUMENTS

| JP | 60-202949 | 10/1985 |
|---|---|---|
| JP | 2-134510 | 5/1990 |
| JP | 6-249791 | 9/1994 |
| JP | 8-210820 | 8/1996 |
| JP | 11-194321 | * 1/2001 |

OTHER PUBLICATIONS

Sakurai et al. "Capture Rate Enhancement Method of 0.1 micro-meter Level Defects by Pattern Matching Inspectors". Oct. 1999. 1999 IEEE International Symposium on Semiconductor Manufacturing Conference Proceedings. pp. 131-134.*

(Continued)

*Primary Examiner*—Jingge Wu
*Assistant Examiner*—Aaron Carter
(74) *Attorney, Agent, or Firm*—Buchanan Ingersoll PC

(57) ABSTRACT

Transforming optical images of a portion including a normal conductor pattern having a surface roughness, a portion subjected to an inspection, and a reference portion to images of electric charges and picking up these as electric signals by an image pick-up device, rendering the optical image including the normal conductor pattern having the surface roughness to a pixel signal by the image pick-up device, controlling a light volume of the optical image so that the pixel signal is saturated or immediately before the saturation, picking up a pixel signal of the portion to be inspected under this light volume, obtaining a differential signal from a pixel signal picked up from the reference portion, and judging an existence of defect from the differential signal, so as to detect defects such as a hiatus of conductor, a short circuit, and a deposition of an extraneous matter on a wafer, on which the normal conductor pattern having the roughened surface, with a high accuracy in processes of forming films and etching in manufacturing a semiconductor device.

12 Claims, 14 Drawing Sheets

U.S. PATENT DOCUMENTS

| | | | | |
|---|---|---|---|---|
| 5,737,090 A | * | 4/1998 | Christopher et al. | 358/3.29 |
| 5,859,698 A | * | 1/1999 | Chau et al. | 356/237.2 |
| 5,905,817 A | * | 5/1999 | Matama | 382/260 |
| 6,040,895 A | * | 3/2000 | Haas | 355/70 |
| 6,096,567 A | * | 8/2000 | Kaplan et al. | 438/14 |
| 6,211,505 B1 | * | 4/2001 | Nagamatsu | 250/205 |
| 6,263,099 B1 | * | 7/2001 | Maeda et al. | 382/149 |
| 2002/0076096 A1 | * | 6/2002 | Silber et al | 382/152 |

OTHER PUBLICATIONS

Onoyama et al. "Solution of In-Line Inspection Problem for Grainy Metal Layers by 'Saturation Effect' of Grayscale". Sep. 2000. IEEE, The Ninth Internation Symposium on Semiconductor Manufacturing, 2000. pp. 203-206.*

Translation of JP 02-134510 to Saito (May 23, 1990), presented in the IDS filed on Feb. 15, 2005.*

* cited by examiner

F I G . 1
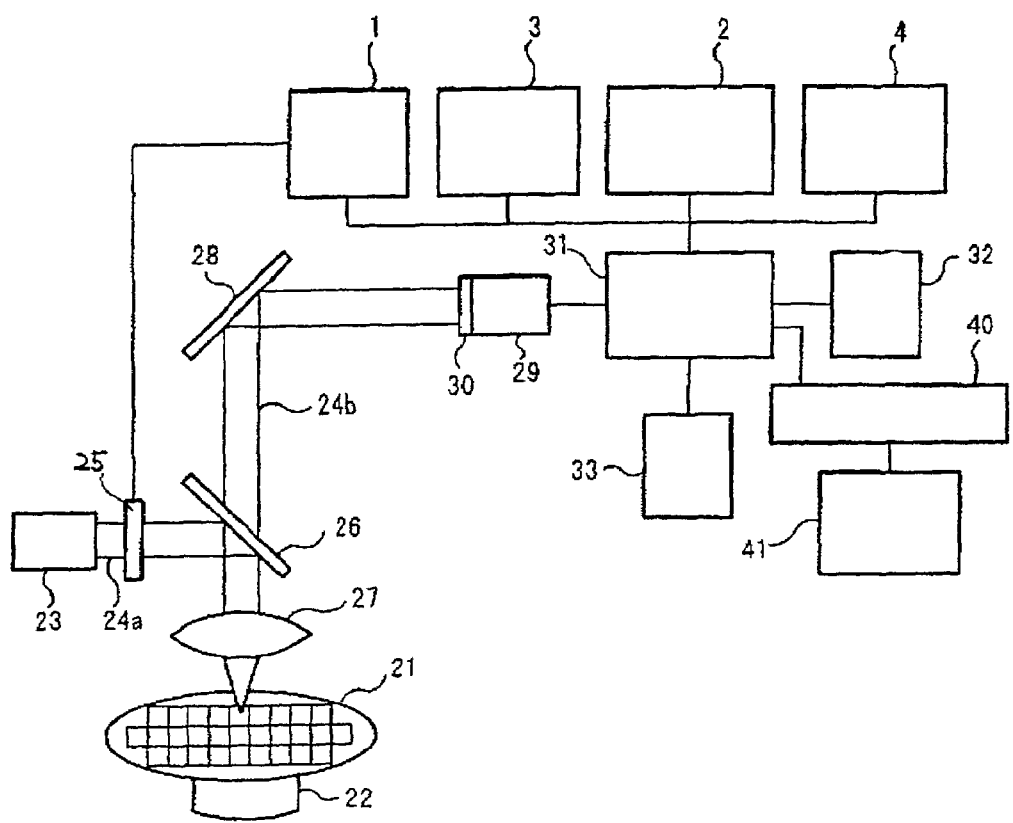

DEFECT INSPECTION METHOD AND DEFECT INSPECTION EQUIPMENT

BACKGROUND OF THE INVENTION

1. Field of the Invention

The present invention relates to a defect inspection method and a defect inspection equipment for inspecting pattern defects and so on in use of an image pick-up device in manufacturing processes and so on of semiconductor devices, in particular, to a method and an equipment for improving detectivity in a case that a surface of a conductor pattern, formed as a film, is extremely rough.

2. Discussion of Background

In a manufacturing process of semiconductor devices, a short-circuit and a hiatus of conductor patterns occur at a time of forming a film and of etching, and reaction byproducts and so on are deposited as extraneous matters, whereby failures of the semiconductor devices occur. In a conventional technique, a defect inspection equipment of an image comparison type, using a white light or a laser beam, is widely used as an equipment effective for inspecting these failures in processes such as film formation and etching. FIG. 12 illustrates a structure of a conventional inspection equipment disclosed in Japanese Unexamined Patent Publication JP-A-60-202949. In the figure, numerical reference 21 designates a wafer to be inspected; numerical reference 22 designates a movable stage; numerical reference 23 designates a light source; numerical reference 24a designates an inspection light; numerical reference 24b designates a reflection light; numerical reference 25 designates an aperture diaphragm; numerical reference 26 designates a half-silvered mirror; numerical reference 27 designates an objective lens; numerical reference 28 designates a mirror; numerical reference 29 designates a camera; numerical reference 30 designates an image pick-up device; numerical reference 31 designates an image processing computer; numerical reference 32 designates an image memory; numerical reference 33 designates a monitor; numerical reference 40 designates a defective address storing unit; and numerical reference 41 designates a determination output unit.

In thus constructed conventional defect inspection equipment, the wafer 21, on which a conductor pattern and so on are formed is located on a movable stage 22, and lighted by the light source 23 in order to manufacture a device. The light emitted from the light source 23 is adjusted by the aperture diaphragm to be an appropriate light volume so as to be the inspection light 24a. The inspection light 24a is turned in a direction of the wafer 21 by the half-silvered mirror 26, converged by the objective lens 27, and introduced into the wafer 21. The reflection light 24b corresponding to various matters on the wafer 21 is enlarged by the objective lens 27, and introduced into the image pick-up device 30, which is integrated in the camera 29, through the half-silvered mirror 26 and the mirror 28. An optical image expressed by intensity of the reflection light 24b is transformed to electric charges by the image pick-up device, and taken out as an electric pixel signal. This electric pixel signal is processed as a picture element pixel signal by the image processing computer 31. The picture pixel signal is compared with reference data, which is previously picked in a similar manner thereto and stored in the image memory 32, and thereafter a defect is judged. An address subjected to the defect determination is stored in the defective address storing unit 40, and the determination is outputted to the determination output unit 41, whereby it is possible to know a position of the defect. Further, it is possible to visually inspect the image by the monitor 33.

In the conventional inspection method in use of the conventional inspection equipment, an inspector ordinarily watches the monitor so that a contrast of an entire inspection image is clear by adjusting the aperture diaphragm 25 to determine appropriate lighting conditions, whereby the image can be recognized. In this case, when a gray image is used, e.g. no pixel signal (darkest) is represented by 0 and saturation of pixel signal (brightest) is represented by 100, an appropriate range is wide enough to be 10 through 90. The optical image taken in the image pick-up device is transformed to the pixel signal within this range. For example, pixel signals of various materials included in an area A of the inspection image data, illustrated in FIG. 13, correspond to values in proportional to illumination reflectances of the materials, wherein a conductor pattern 34 is 80; an oxide film 38 is 25; a short-circuit 35 of the conductor pattern is 80; a hiatus 36 is 25; a deposited conductive extraneous matter 37 is about 60. Pixel signals of a conductor pattern in an area (not shown) similar to that in the reference image data without defects and of an oxide film are respectively about 80 and 25. Accordingly, absolute values of pixel signal differences from the image data including defects are large at positions where defects exist. Therefore, it is possible to judge that the address has the defects.

However, according to a recent trend, an aluminum film and so on are formed by sputtering, wherein a grain boundary with harsh roughness, called a grain, is formed on a surface of the film to reduce an illumination reflectance at this portion. Therefore, a pixel signal difference from the defect such as a hiatus of conductive pattern is decreased, whereby it becomes difficult to judge whether the pattern is normal or defective. Thus, there are cases that inspection equipments do not properly function.

A specific example of the cases will be described in reference of figures. FIG. 14a through 14d illustrate a specific example of the conventional inspection method. FIG. 14a illustrates an example of reference image data stored in the pick-up image memory 32 in an image area A, and FIG. 14c illustrates a pixel signal at a position R. FIG. 14b illustrates an inspection image data including defects, picked up from the image area A, and FIG. 14d illustrates a pixel signal at a position E corresponding to the position R, and a differential pixel signal between the position E and position R. In FIG. 14a, numerical reference 34a designates a conductor pattern without roughness, and numerical reference 38 designates an oxide film, of which pixel signals are, for example, about 80 and about 25 as in FIG. 14c. In FIG. 14b, numerical reference 34a designates a conductor pattern without roughness; numerical reference 34b designates a roughened portion, in which grains are formed; numerical reference 38 designates an oxide film; numerical reference 35 designates a short-circuit of the conductor; numerical reference 36 designates a hiatus of the conductor; numerical reference 37 designates a deposited conductive extraneous matter, of which pixel signals respectively are about 80, 35, 25, 80, 25, and 60 as in FIG. 14d. In FIG. 14d, a result of an operation of a differential pixel signal between the inspection image data in FIG. 14b and the reference image data in FIG. 14a is shown. For example, when a threshold value for judging defect is set to be 15 to judge whether or not an absolute value of the differential pixel signal exceeds the threshold value, the grain 34b, being a normal conductor pattern, is also judged defective because values corresponding to the short-circuit, the hiatus, and the conductive extraneous matter exceed the threshold value, and an absolute value of the differential pixel signal corresponding to the grain 34b exceeds the threshold value.

Further, also in a case that a conductor pattern is deliberately formed so as to be roughened in order to increase a surface area of a roughened surface capacitor, an illumination reflectance is decreased, whereby there is a problem that a normal pattern cannot be recognized. Also in this case, there are a drawbacks that a normal device is scraped judged defective and scrapped because a normal portion is judged defective or that a failure should be further judged by an inspection using an electric pixel signal after entire processes without inspecting in processes for film formation, etching, and so on. Further, when process conditions, such as a temperature and a gas quantity, are newly studied, it is impossible to evaluate a defect incidence by a visual inspection in the processes.

SUMMARY OF THE INVENTION

It is an object of the present invention to solve the above-mentioned problems inherent in the conventional technique and to provide an inspection method and an inspection equipment, by which short-circuits, hiatuses, deposited extraneous matters, and so on in a conductor pattern, produced in processes of film formation, etching, and so on, can be detected as defects at high probability even though a surface of the conductor pattern is deliberately roughened or has grains.

According to a first aspect of the present invention, there is provided a defect inspection method comprising:

a first step of setting an initial value in a light volume of an inspection light illuminating an object to be inspected and picking up an inspection image;

a second step of selecting a normal pattern portion having a roughened surface out of the picked up image and picking up an optical image of the normal pattern portion as a pixel signal in use of an image pick-up device;

a third step of controlling the light volume so that the pixel signal is saturated or immediately before saturation;

a fourth step of picking up a pixel signal of a portion to be inspected and a pixel signal of a reference portion, corresponding to the portion to be inspected, under the controlled light volume; and a fifth step of judging an existence of a defect in use of a differential signal between the pixel signal of the portion to be inspected and the pixel signal of the reference portion.

According to a second aspect of the present invention, there is provided the defect inspection method according to the first aspect of the invention, further comprising:

a numerically processing step of decreasing a level of the pixel signals, which level is increased by increasing the light volume, and amplifying the pixel signals, wherein the numerical processing step is interposed between the fourth and fifth steps.

According to a third aspect of the present invention, there is provided a defect inspection device comprising:

a light source illuminating an object to be inspected;

a diaphragm aperture for adjusting a light volume of an inspection light;

an image pick-up device introducing the inspection light from the object to be inspected, transforming an optical image formed by the inspection light into electric charges, and picking up as an electric signal;

an image processing computer for processing the electric signal as a pixel signal of an image;

an image memory holding a reference image, which is compared with the inspection image;

a pixel signal pick-up unit selecting and picking up a normal pattern portion having a roughened surface as a pixel signal;

a pixel signal judging unit for judging whether or not the pixel signal is saturated or immediately before the saturation; and a light volume control unit instructing an increment of the light volume to the diaphragm aperture in accordance with the judgment by the pixel signal judging unit.

According to a fourth aspect of the present invention, there is provided the defect inspection device according to the third aspect of the invention, further comprising:

a pixel signal processing unit for numerically processing to reduce a level of the pixel signal, increased by the increment of the light volume, and to amplify the pixel signal.

According to a fifth aspect of the invention, there is provided a defect inspection method, by which an image pick-up device for transforming an optical image to electric charges and picking up as electric pixel signals, wherein an optical image including a normal conductor pattern having a roughened surface is changed to pixel signals, a light volume of the optical image is controlled so that the pixel signals are saturated or just before the saturation, pixel signals corresponding to a portion to be inspected are picked up under the light volume, and an existence of a defect is judged in use of differential signals between the pixel signals, picked out of the portion to be inspected, and pixel signals picked out of a reference portion.

According to a sixth aspect of the present invention, there is provided a defect inspection method, wherein an optical image including a normal conductor pattern having a roughened surface is changed to pixel signals by an image pick-up device, a light volume of the optical image is controlled so that the pixel signals are saturated or just before the saturation, the light volume is determined, a lower limit value of the pixel signals is decreased by adjusting an entire portion of pixel signals to be inspected, the pixel signals are amplified, the light volume is again controlled in use of a part of the pixel signals corresponding to the conductor pattern having the roughened surface, a pixel signal difference is increased by a numerical process of multiplying an increment of the light volume, an existence of a defect is judged in use of differential signals between pixel signals picked out of a portion to be inspected and pixel signals picked out of a reference portion.

According to a seventh aspect of the present invention, there is provided a defect inspection device comprising: an image pick-up device for transforming optical images of a portion of a conductor pattern having a roughened surface, of a portion to be inspected, and of a reference portion and picking up as electric pixel signals; a pixel signal pick-up unit rendering the optical image of the portion of the conductor pattern having the roughened surface pixel signals in use of the image pick-up device; a pixel signal judging unit for judging the pixel signals such that the pixel signal is saturated or just before the saturation; and a light volume control unit for controlling a light volume of the optical image in receipt of the pixel signal from the pixel signal judging unit.

According to an eighth aspect of the present invention, there is provided a defect inspection equipment according to the third aspect of the invention further comprising: a pixel signal processing unit performing a numerical process to reduce a level of the pixel signal, which is increased by an increment of the light volume, and to amplify the pixel signal.

BRIEF DESCRIPTION OF THE DRAWINGS

A more complete appreciation of the invention and many of the attendant advantages thereof will be readily obtained as the same becomes better understood by reference to the following detailed description when considered in connection with the accompanying drawings, wherein:

FIG. 1 schematically illustrates a structure of a defect inspection equipment according to the present invention;

FIG. 14c is a graph showing a pixel signal at a position R in FIG. 14a; and

DETAILED DESCRIPTION OF THE PREFERRED EMBODIMENTS

Figure 2:
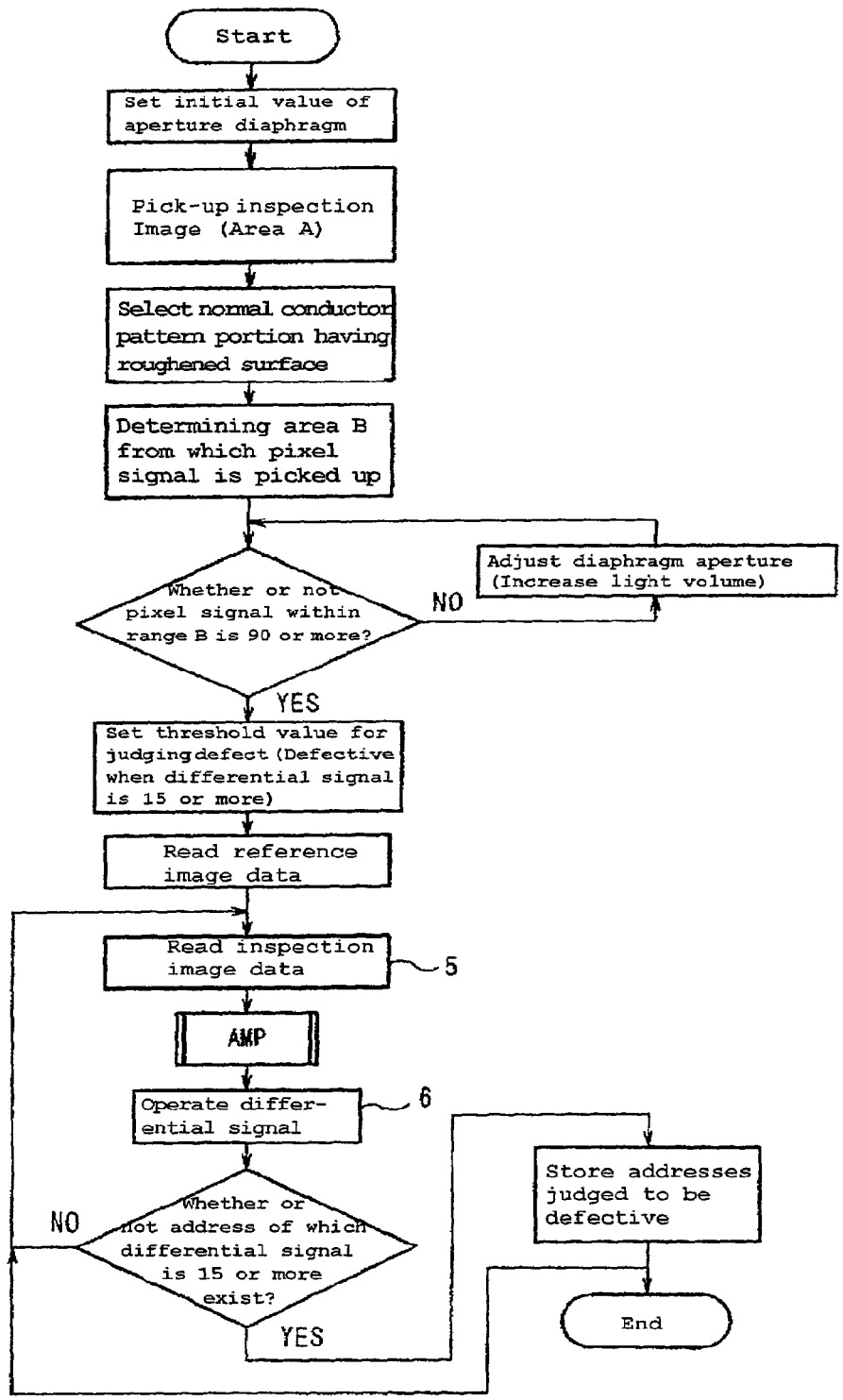
FIG. 2 is a flow chart showing a procedure of a defect inspection method according to Embodiment 1 of the present invention.

A detailed explanation will be given of preferred embodiments of the present invention in reference to FIGS. 1 through 11 as follows, wherein the same numerical reference is used for the same or similar portion and description of these portion is omitted.

Embodiment 1

FIG. 1 schematically illustrates a structure of a defect inspection equipment according to Embodiment 1 of the present invention. In FIG. 1, numerical reference 1 designates a light volume controlling unit; numerical reference 2 designates a pixel signal pick-up unit; numerical reference 3 designates a pixel signal judging unit; numerical reference 4 designates a pixel signal processing unit; numerical reference 21 designates a wafer; numerical reference 22 designates a movable stage; numerical reference 23 designates a light source; numerical reference 24a designates an inspection light; numerical reference 24b designates a reflection light; numerical reference 25 designates an aperture diaphragm; numerical reference 26 designates a half-silvered mirror; numerical reference 27 designates an objective lens; numerical reference 28 designates a mirror; numerical reference 29 designates a camera; numerical reference 30 designates an image pick-up device; numerical reference 31 designates an image processing computer; numerical reference 32 designates an image memory; numerical reference 33 designates an image monitor; numerical reference 40 designates a defective address storing unit; and numerical reference 41 designates judgment output unit.

In thus constructed defect inspection equipment according to Embodiment 1, in a similar manner to that in the conventional defect inspection equipment, the wafer 21, on which a conductor pattern and so on are formed, is mounted on the movable stage 22 and illuminated by the light source 23 in order to produce a device. The light generated by the light source 23 is adjusted to have an appropriate light volume by the diaphragm aperture 25 and served as the inspection light 24a. The inspection light 24a is bent in a direction toward the wafer 21 by the half-silvered mirror 26, converged by the objective lens 27, and introduced into the wafer 21. The reflection light 24b corresponding to various materials on the wafer 21 is enlarged by the objective lens 27, and introduced into the image pick-up device 30 built in the camera 29 through the half-silvered mirror 26 and the mirror 28. An optical image, expressed by an intensity of the reflection light 24b, is converted to electric charges by the image pick-up device 30, and picked up as an electric pixel signal. The electric pixel signal is processed as an image pixel signal by the image processing computer 31, and compared with reference data, which are previously collected in a manner similar thereto and stored in the image memory 32, to judge an existence of a defect. An address judged defective is stored in the defective address storing unit 40, and the judgment is outputted to the determination output unit 41, whereby it is possible to know a position where the defect exists. Further, it is also possible to visually inspect the image from the monitor 33.

A defect inspection method according to Embodiment 1 in use of the defect inspection equipment will be described in reference of the figures. FIG. 2 is a flow chart explaining a defect inspection process according to Embodiment 1 wherein numerical reference 101 designates "start"; numerical reference 102 designates a step of setting an initial value of an aperture diaphragm;

numerical reference 103 designates a step of picking up an inspection image from an area A; numerical reference 104 designates a step of selecting a normal conductor pattern portion having a roughened surface; numerical reference 105 designates a step of determining an area B, from which a pixel signal is picked; numerical reference 106 designates a step of judging whether or not the pixel signal within the range B is 90 or more; numerical reference 107 designates a step of adjusting the diaphragm aperture by increasing a light volume; numerical reference 108 designates a step of setting a threshold value for judging a defect, wherein it is judged defective when a differential signal is 15 or more; numerical reference 109 designates a step of reading reference image data; numerical reference 5 designates a step of reading inspection image data; numerical reference 110 designates a step of amplifying; numerical reference 6 designates a step of operating the differential signal; numerical reference 111 designates a step of judging whether or not an address, of which differential signal is 15 or more, exists; numerical reference 112 designates a step of storing the address judged to defective; and numerical reference 113 designates "End".

Figure 3:
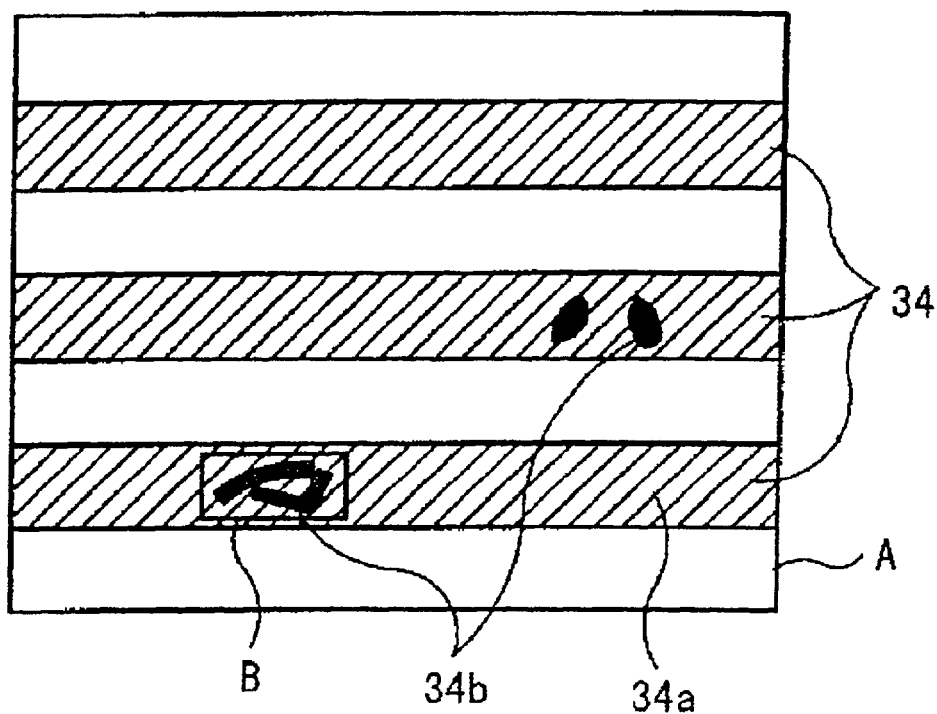
FIG. 3 is a plan view showing an area, which is picked up as a pixel signal for controlling a light volume according to the present invention.

FIG. 3 is a plan view illustrating an example of an inspection area and an area, from which pixel signal is picked up for controlling a light volume according to Embodiment 1, wherein a reference A designates an inspection image area, a reference B designates the area, from which the pixel signal is picked up; numerical reference 34 designates a conductor pattern; numerical reference 34*a* designates a portion without a roughened portion; and numerical reference 34*b* designates a roughened portion.

In the defect inspection equipment constructed as in FIG. 1, when the defect inspection method according to Embodiment 1 is applied, a pixel signal of the image area A illustrated in FIG. 3 is picked out of the wafer 21 as illustrated in FIG. 2. The pixel signal pick-up area B including a normal conductor pattern and the roughened portion 34*b* is set within the image area A, and the pixel signal pick-up area B is picked up into the pixel signal pick-up unit 2. Because the pixel signal of the area B includes the portion 34*a* without the roughened portion and the roughened portion 34*b* on the conductor pattern, the pixel signal has values, for example, about 80 and 35. In the pixel signal judging unit 3, it is judged whether or not all of the pixel signals are, for example, 90 or more, being immediately before a saturation pixel signal. When the pixel signal does not reach 90, an instruction is sent to the light volume controlling unit 1 to adjust the diaphragm aperture 25 in order to increase the light volume. This process is repeated until all of the pixel signals within the range B become 90 or more.

Reference image data and inspection image data are read under the increased light volume, a differential pixel signal between these is obtained, a defect is judged when the differential pixel signal is a defect judgment threshold value or more, and a corresponding address is stored in the defective address storing unit. When the inspection image data are plural, the inspection image data are again read under the same light volume, and a similar process is repeated.

Figure 4:
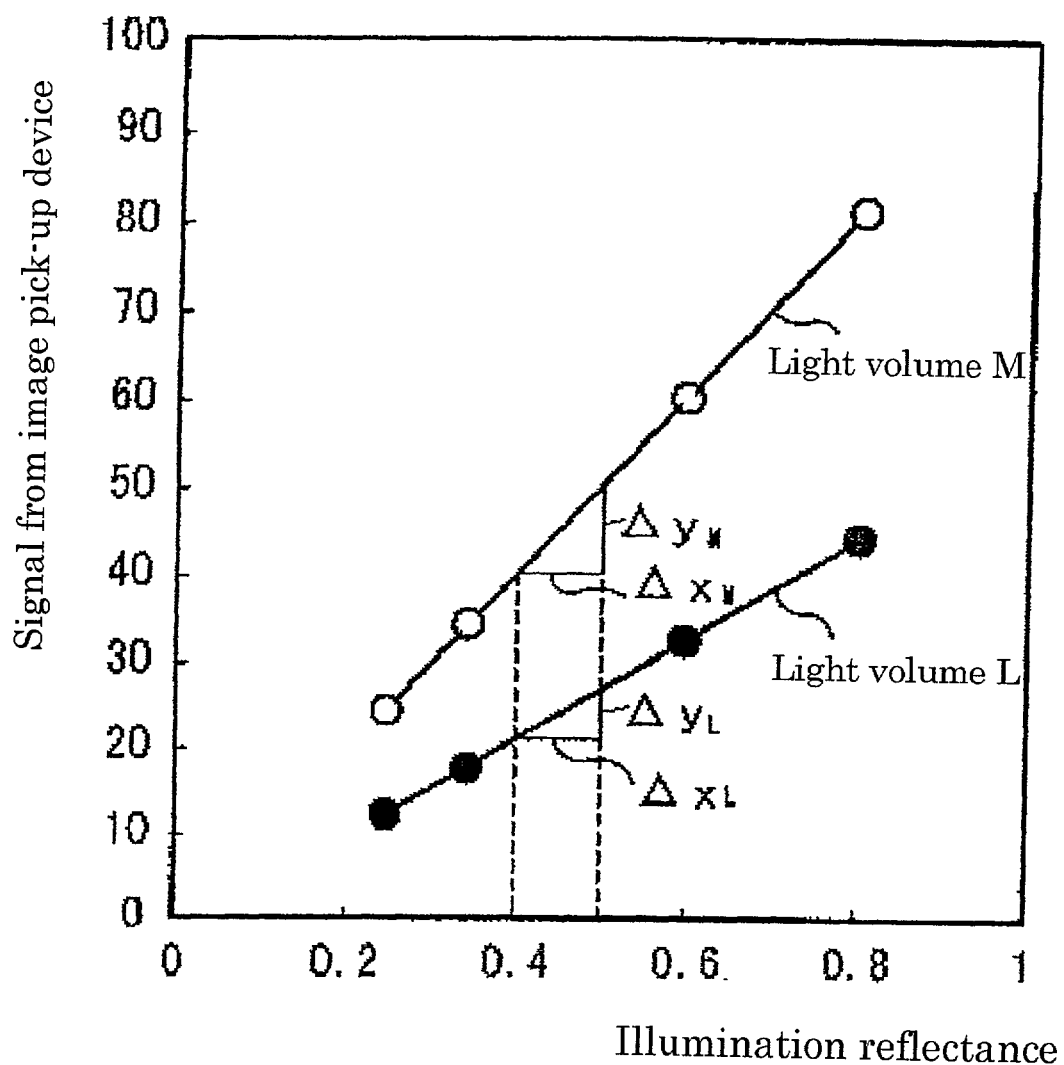
FIG. 4 is a graph showing a relationship between pixel signals from an image pick-up device and illumination reflectances according to the present invention.
Figure 5:
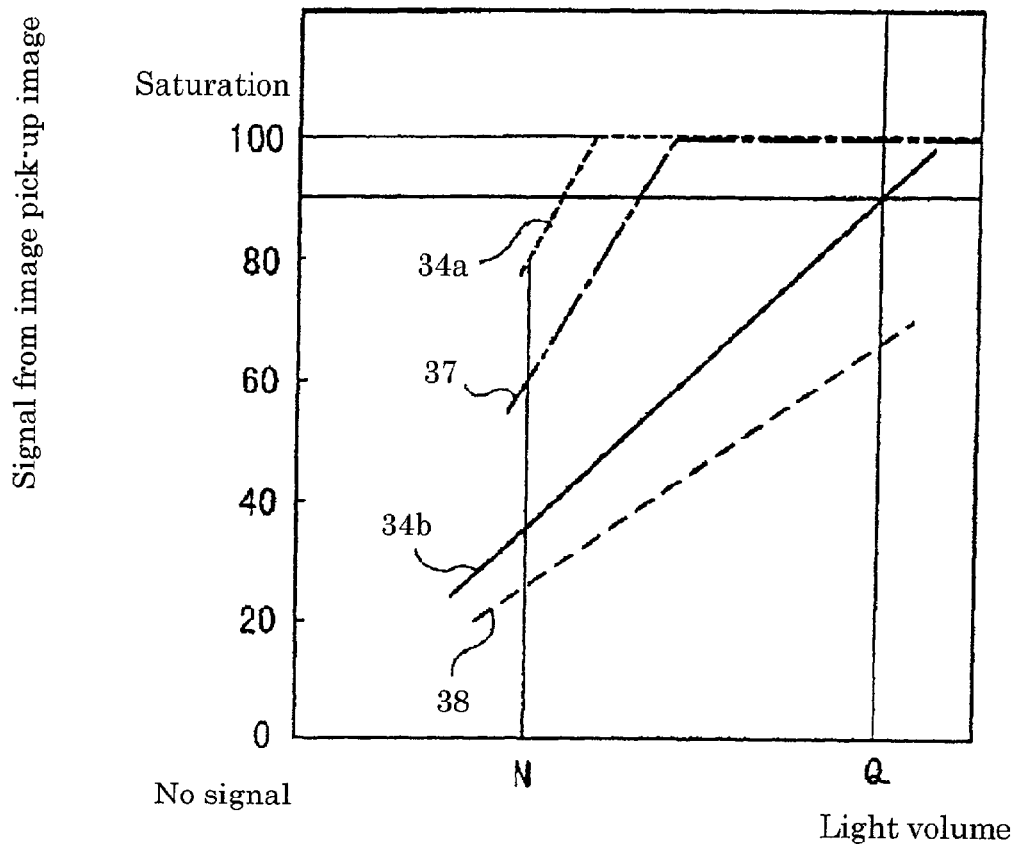
FIG. 5 is a graph showing a relationship between the pixel signals from the image pick-up device and light volumes.

A transition of the pixel signal of a material to be inspected in the process of controlling the light volume will be described in detail in reference of figures. FIG. 4 is a graph showing a relationship between the pixel signal picked up by the image pick-up device 30 and an illumination reflectance of the material to be inspected. FIG. 5 is a graph showing a relationship between the pixel signal and the light volume, whereby a principle for determining a pixel signal level, judged and compared by the pixel signal judging unit 3, is explained.

An optical image picked up in the image pick-up device 30 is expressed by multiplying an illumination reflectance of a material on the wafer 21 by the illuminating light volume. Therefore, as illustrated in FIG. 4, a slant of a line in the relationship between the pixel signal and the illumination reflectance increases as the light volume increases. For example, when a light volume M is larger than a light volume L, the slant $\Delta yM/\Delta xM$ of a line under the light volume M becomes larger than a slant $\Delta yL/\Delta xL$ of a line under the light volume L. Accordingly, it is possible to increase a pixel signal difference between various materials by increasing the light volume. When the light volume is further increased, and exceeds a certain level, the image pick-up device is saturated, whereby the pixel signal does not exceed a certain value, for example, 100. Accordingly, as illustrated in FIG. 5, when the pixel signal of the roughened portion 34*b* in the conductor pattern is set to be 90 immediately before the saturation, the pixel signal of the portion 34*a* without the roughened portion in the conductor pattern is already saturated to be 100, whereby the difference can be reduced.

Further, when the light volume Q controlled according to Embodiment 1 and illustrated in FIG. 5, a pixel signal of a conductive extraneous matter 37 is 100, and a pixel signal of an oxide film 38, being an insulating material, is about 65.

Figure 6A:
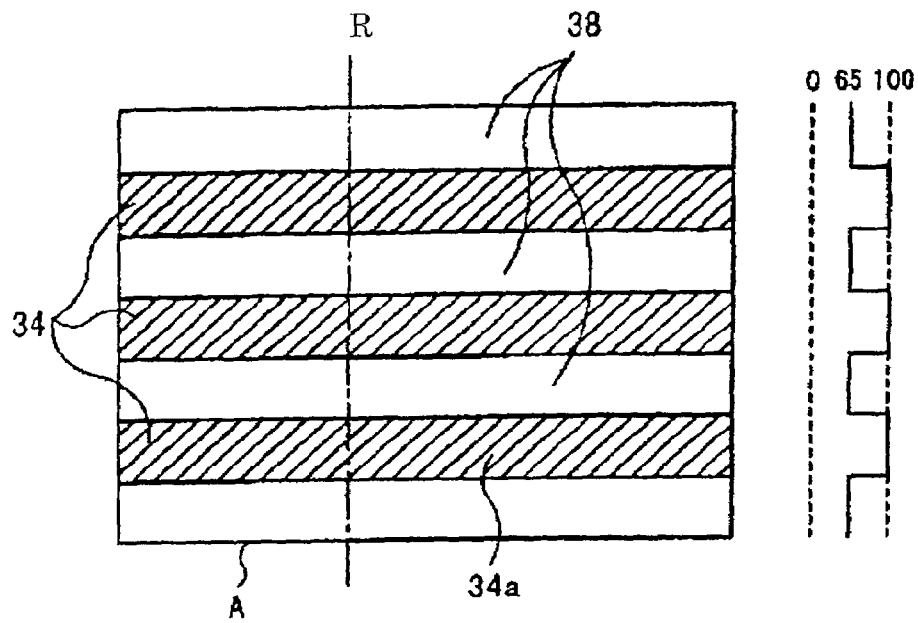
FIG. 6a is a plan view illustrating a reference image and an inspection image in accordance with Embodiment 1 of the present invention.
Figure 6C:
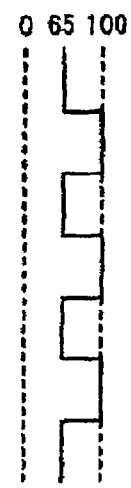
FIG. 6c is a graph showing a pixel signal at a position R in FIG. 6a under a light volume Q.
Figure 6B:
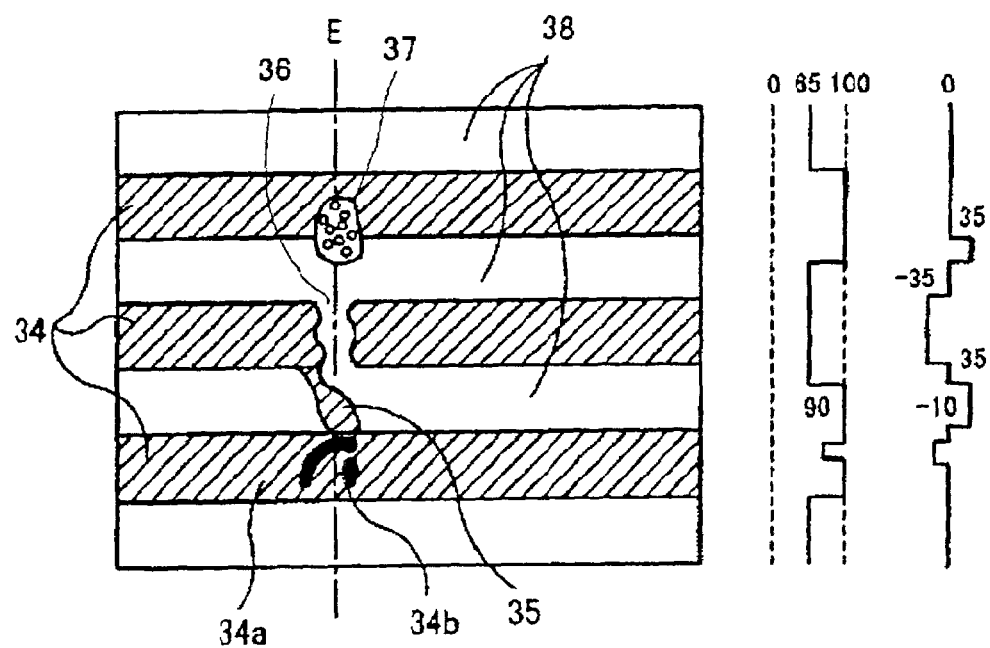
FIG. 6b is a plan view illustrating the reference image and the inspection image in accordance with Embodiment 1 of the present invention.
Figure 6D:
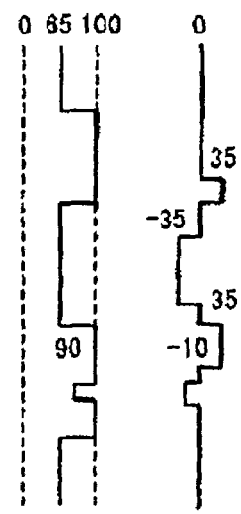
FIG. 6d is graphs showing a pixel signal at a position E in FIG. 6b under the light volume Q and a differential signal between the position R in FIG. 6b and the position E in FIG. 6b.

Further, FIGS. 6*a* through 6*d* illustrate examples of specific reference image data and inspection image data, picked up in accordance with the defect inspection method according to Embodiment 1. FIG. 6*a* illustrates reference image data, picked up from the image area A and stored in the image memory 32, and FIG. 6*c* illustrates an example of a pixel signal of a position R under the light volume Q, obtained by the above-mentioned light volume control. FIG. 6*b* illustrates inspection image data including defects picked up from the image area A, and FIG. 6*d* illustrates a pixel signal at a position E corresponding to the position R, and a differential pixel signal between the positions E and R. In FIG. 6*a*, numerical reference 34*a* designates a portion on the conductor patterned without a roughened portion; and numerical reference 38 designates an oxide film, wherein, for example, pixel signals are respectively about 10 and 65 as in FIG. 6*c*. In FIG. 6*b*, numerical reference 34 designates a conductor pattern; numerical reference 34*a* designates a portion without a roughened portion; numerical reference 34*b* designates a roughened portion having a grain; numerical reference 38 designates an oxide film; and numerical references 35, 36, and 37 designate defects, wherein numerical reference 35 designates a conductor short-circuit; numerical reference 36 designates a hiatus of conductor; numerical reference 37 designates a deposited conductive extraneous matter, wherein pixel signals thereof are respectively about 100, 90, 65, 100, 65, and 100 as in FIG. 6*d*. Operating a differential pixel signal of the pixel signals of the inspection image data in FIG. 6*d* and the difference image data in FIG. 6*c* provides a graph in FIG. 6*d*. For example, the defect judgment threshold value is set to be 15, and it is judged whether or not an absolute value of a differential pixel signal exceeds the threshold value or not. The conductor short-circuit, the hiatus, and the conductive extraneous matter are judged defective because the absolute values of the differential pixel signals are 35, larger than the threshold value 15. The grain 34b is judged normal because the absolute value of the differential pixel signal of the grain 34b, being a normal conductor pattern, is 10, smaller than the threshold value. Thus, an accurate judgment is obtainable.

Figure 7:
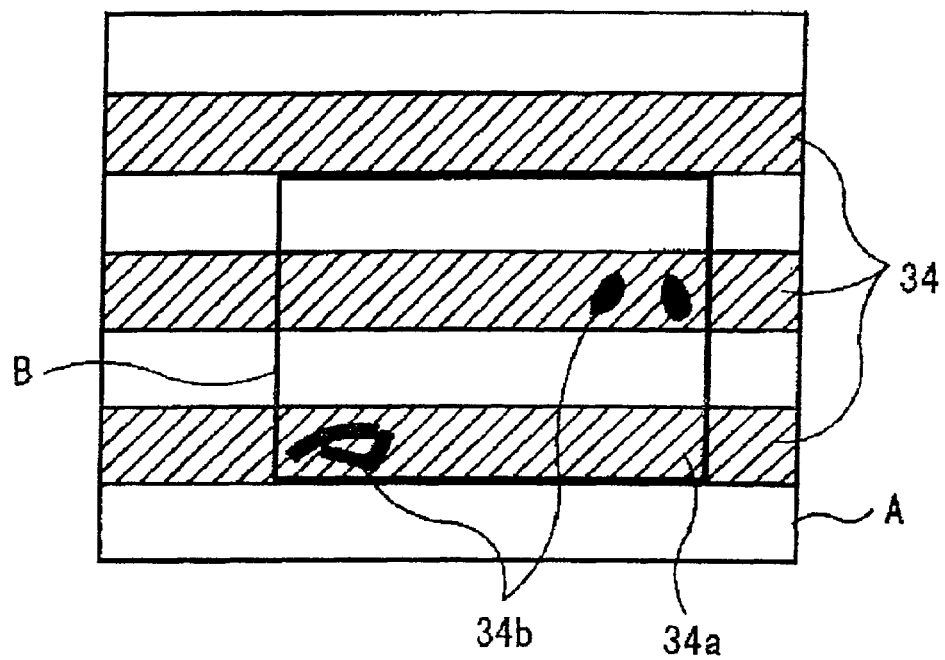
FIG. 7 is a plan view illustrating an area, from which a pixel signal for controlling a light volume is picked up, according to another mode of the present invention.
Figure 8:
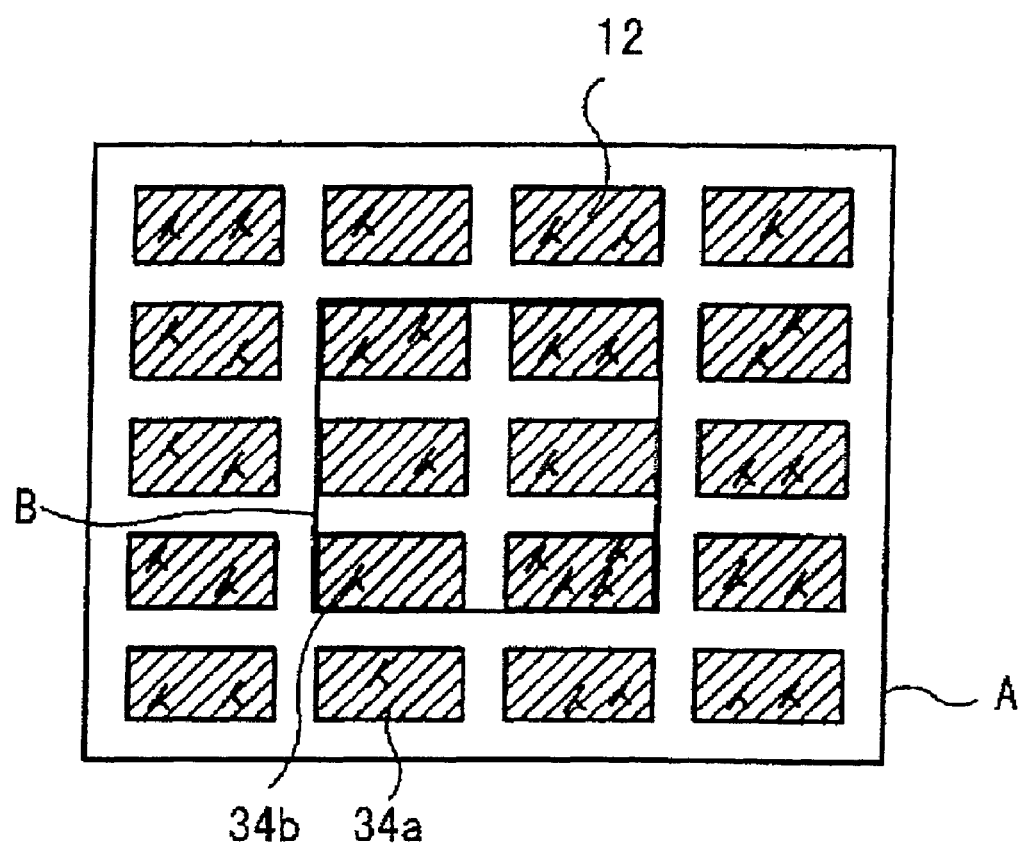
FIG. 8 is a plan view illustrating an area, from which a pixel signal for controlling a light volume is picked up, according to another mode of the present invention.

In Embodiment 1, although, the pixel signal pick-up area B to be processed is a part on a single conductor pattern illustrated in FIG. 3, and all of the pixel signals are rendered 90 or more immediately before the saturation in a process of determining the light volume, for example, when the pixel signal pick-up area B illustrated in FIG. 7 is used, the width of the conductor pattern and the width of the oxide film are the same in a 1 to 1 proportion so that an area ratio occupied by the conductor pattern is 50%. Therefore, by determining a judgment standard such that 50% or more of the pixel signals within the pixel signal pick-up area B becomes 90 or more, it is possible to easily set the pixel signal pick-up area B with respect to a minute pattern. Even though the proportion between the widths of the conductor pattern and the oxide film is not 1 to 1, it is possible to judge in consideration of the area ratio of the conductor pattern.

Further, although the example that the inspection area A includes a linear pattern formed by repeatedly arranging conductors and oxide films as illustrated in FIG. 3 is described, the defect inspection method and the defect inspection equipment according to Embodiment 1 are applicable to a semiconductor device, formed by arranging cells 12, on which a conductor pattern including a grain 34b is formed, like a lattice and/or a pixel signal pick-up area B including some of the cells.

Further, although the example that the light volume is adjusted by the diaphragm aperture is described, it is possible to locate a rotatable filter and so on, for example, having a continuously changing transmittance, for the diaphragm aperture 25, whereby the pixel signal of the pixel signal pick-up area B can be set immediately before the saturation pixel signal in use of the light volume controlling unit 1.

Further, by adjusting the light volume of the light source itself in use of the light volume controlling unit 1, the pixel signal of the pixel signal pick-up area B can be set immediately before the saturation signal.

Embodiment 2

Figure 9:
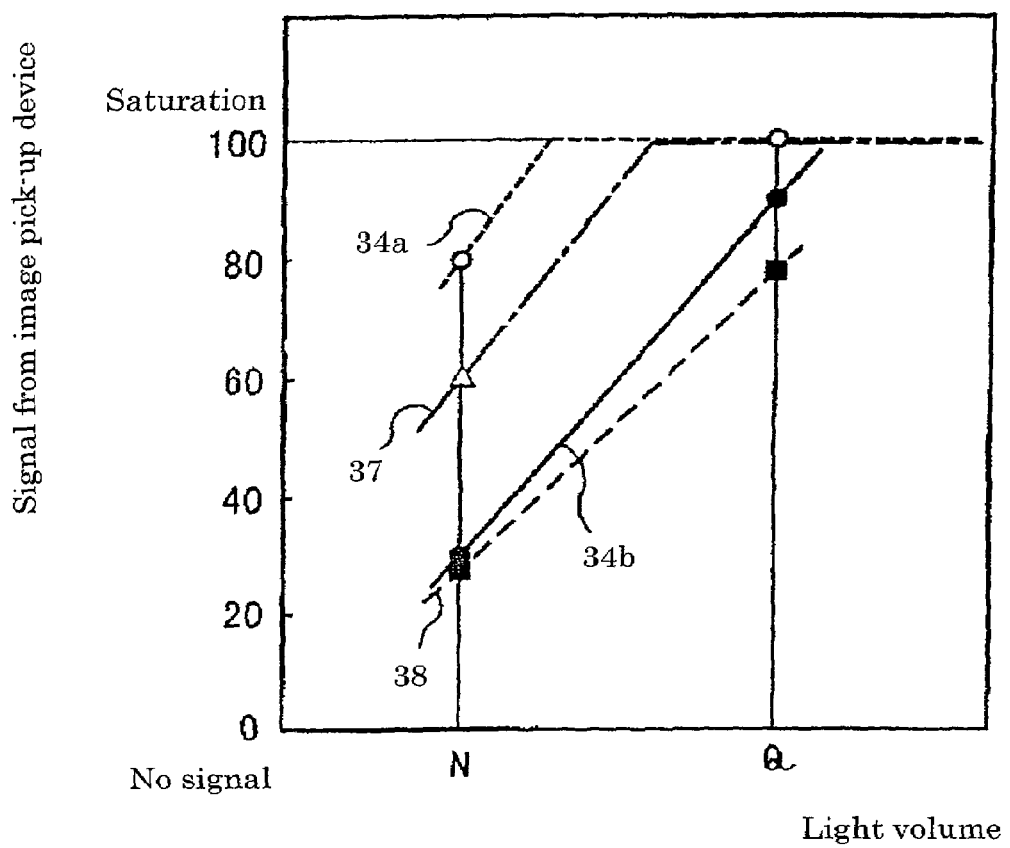
FIG. 9 is a graph showing a relationship between pixel signals from an image pick-up device and light volumes according to Embodiment 2 of the present invention.

Although in Embodiment 1, the example of the defect inspection method including steps of increasing the light volume so that the pixel signal of the pixel signal pick-up area B is immediately before the saturation, of picking up the optical image of the inspection image area A under the light volume, of reducing the pixel signal difference between the portion 34a without the roughened portion on the conductor pattern and the roughened portion 34b on the conductor pattern, and of increasing the pixel signal difference from the oxide film 38 particularly for detecting the hiatus 36 of the conductor is described, a method of inspecting a defect applicable to a case that a pixel signal difference is further reduced will be described. For example, in Embodiment 1, the example that the pixel signal of the roughened portion 34b is 35 and the pixel signal of the oxide film 38 is 25 is described, when the values respectively have a variation of about ±3 and a roughened portion 34b is 32 and an oxide film 38 is 28, a pixel signal difference under a light volume N becomes extremely small as illustrated in FIG. 9. By increasing the light volume to Q, the pixel signal difference between the roughened portion 34b and the oxide film 38 is increased. However, a pixel signal difference between a portion 34a without the roughened portion and the roughened portion 34b, and a pixel signal difference between the roughened portion 34b and the oxide film 38 are both about 10, whereby it is impossible to clarify a difference between the normal portion 34b and a defective hiatus 36 of the conductor, corresponding to the oxide film. Therefore, the width of the pixel signal is increased by numerically processing the pixel signal picked up under the light volume Q, by, for example, the pixel signal processing unit 4 illustrated in FIG. 1 in use of the following Equations 1 and 2 to decrease a level.

$$\text{New pixel signal value} = c \times \text{current pixel signal value} - d, \quad \text{(Equation 1)}$$

when $0 \leq$ current pixel signal value $< 90$, wherein provided that new pixel signal value$<0$, new pixel signal value$=0$ $$\text{New pixel signal value} = \text{current pixel signal value}, \quad \text{when } 90 \leq \text{current pixel signal value} \quad \text{(Equation 2)}$$

Although the references c and d in Equation 1 are not specified, it is preferable to render pixel signal values of at least the roughened portion on the conductor pattern and the oxide film are about 10 or more and 90 or less. For example, when c=2 and d=100, the above-mentioned two pixel signals are amplified to be two times as much, wherein the pixel signal values are settled within the above-mentioned range. However, it is not preferable to render other pixel signal values 0 or less in this process. Therefore, when the pixel signal value is 0 or less, it is changed to 0. Succeedingly, the light volume is again increased to determine a light volume P, where the pixel signal of the roughened portion 34b is 90 being immediately before the saturation, and an operation is conducted based on the following Equations 3 and 4, wherein the pixel signals are numerically processed by multiplying the increment of the light volume.

$$\text{New pixel signal value} = \text{current pixel signal value} \times \text{current light volume/previous light volume}, \quad \text{when current pixel signal value} < 100 \quad \text{(Equation 3)}$$

$$\text{New pixel signal value} = \text{current pixel signal value}, \quad \text{when current pixel signal value} \geq 100 \quad \text{(Equation 4)}$$

Figure 10:
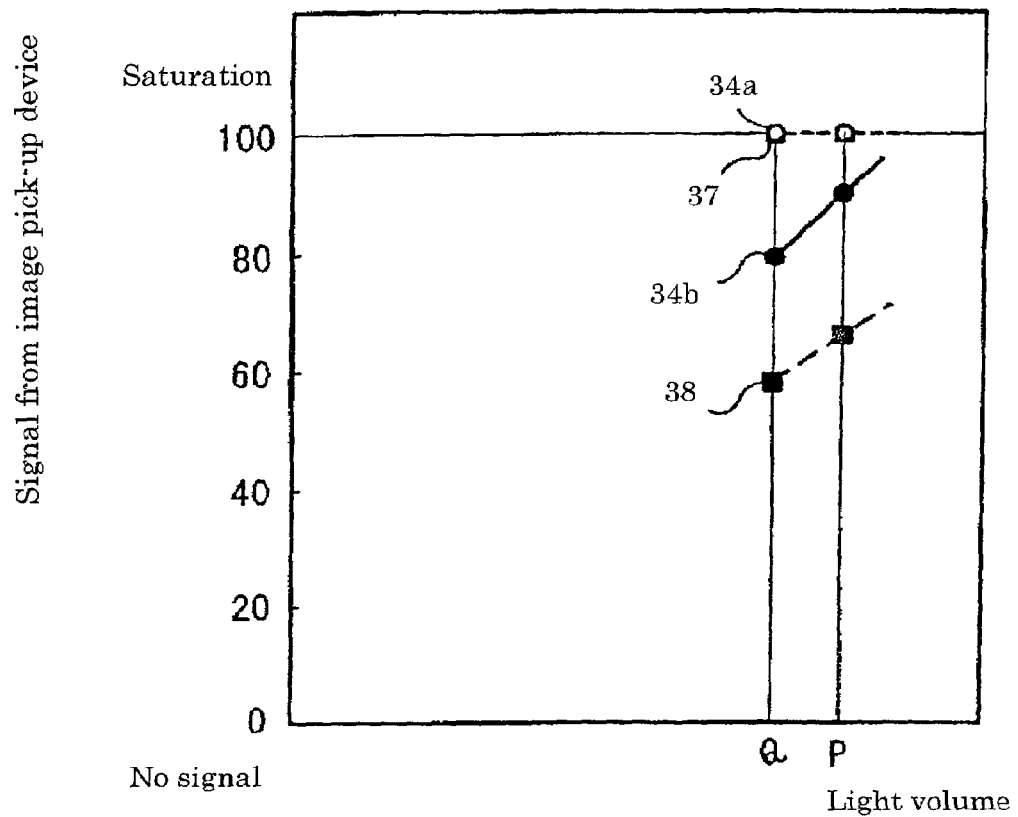
FIG. 10 is a graph showing a relationship between the pixel signals from the image pick-up device and light volumes according to Embodiment 2 of the present invention.
Figure 11:
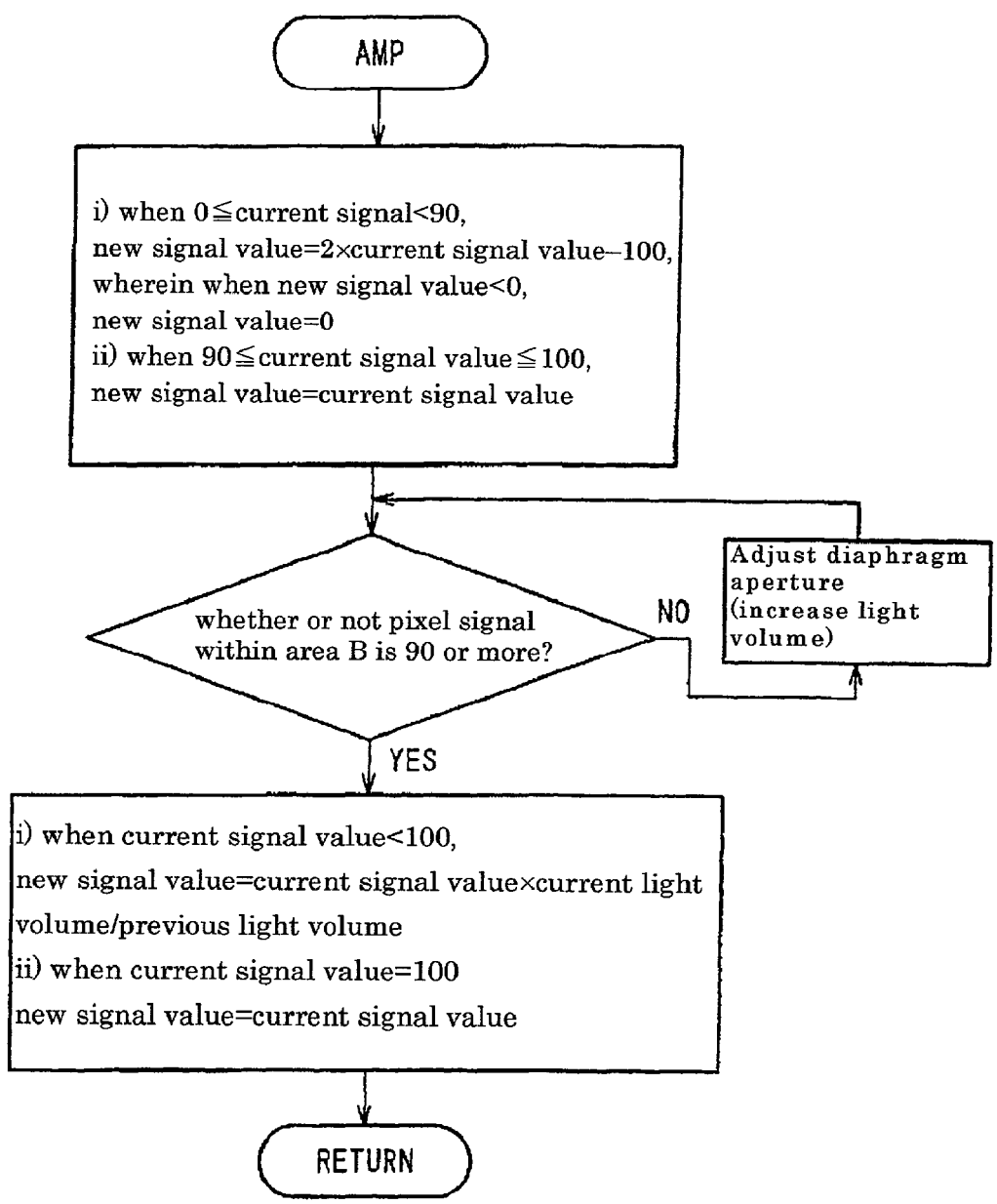
FIG. 11 is a flow chart showing a part of a procedure of a defect inspection method according to Embodiment 2 of the present invention.
Figure 12:
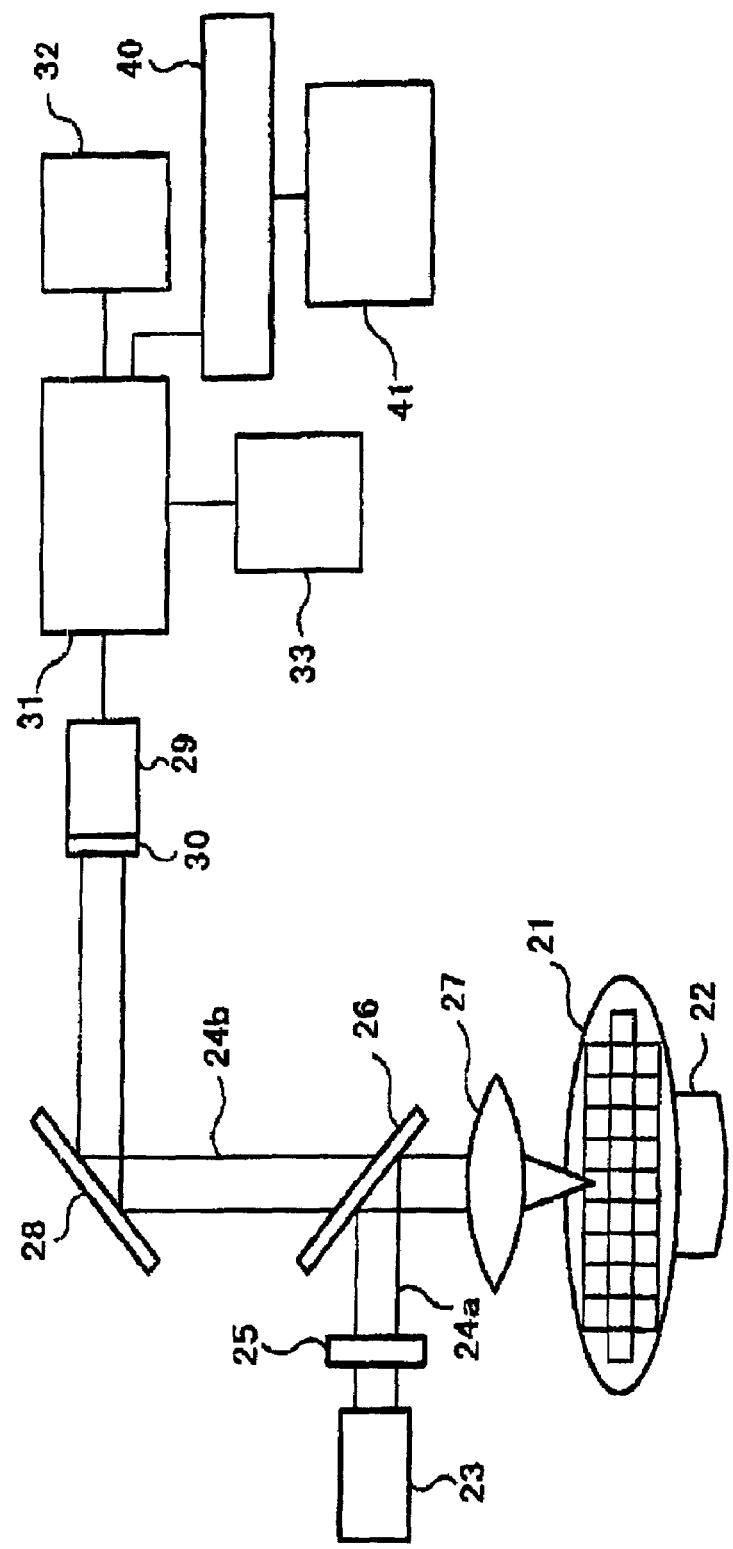
FIG. 12 schematically illustrates a structure of a conventional defect inspection equipment.
Figure 13:
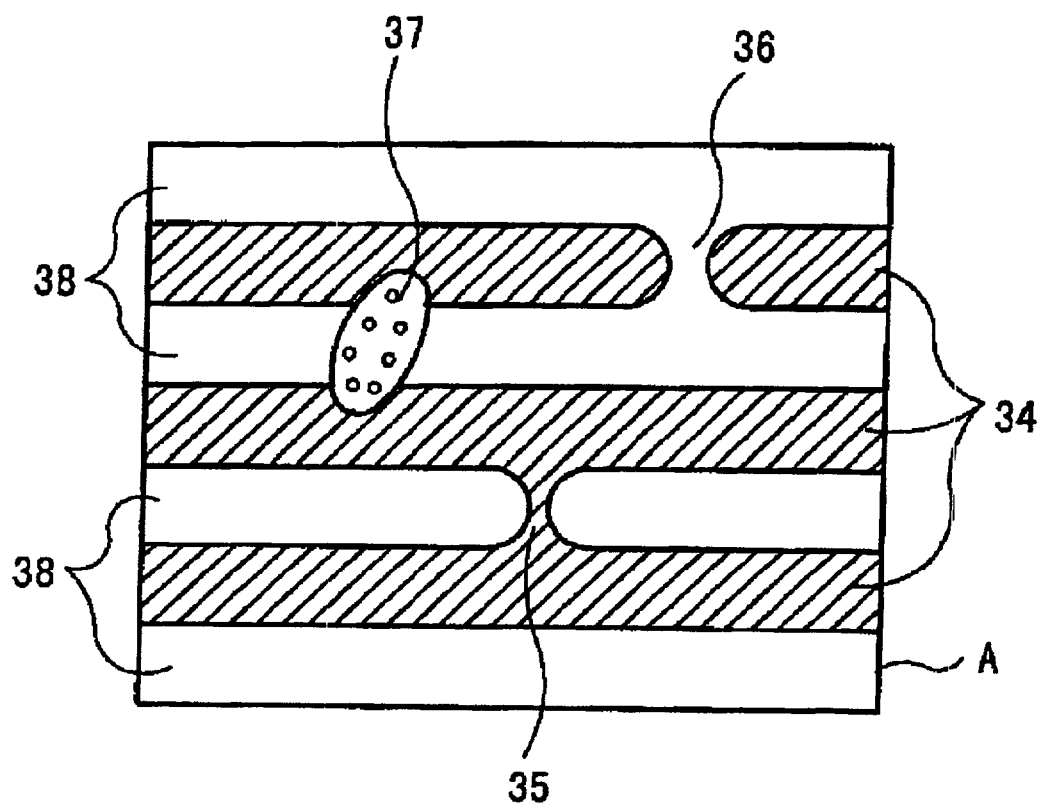
FIG. 13 is a plan view showing examples of defects, which are inspected in a conventional technique.
Figure 14A:
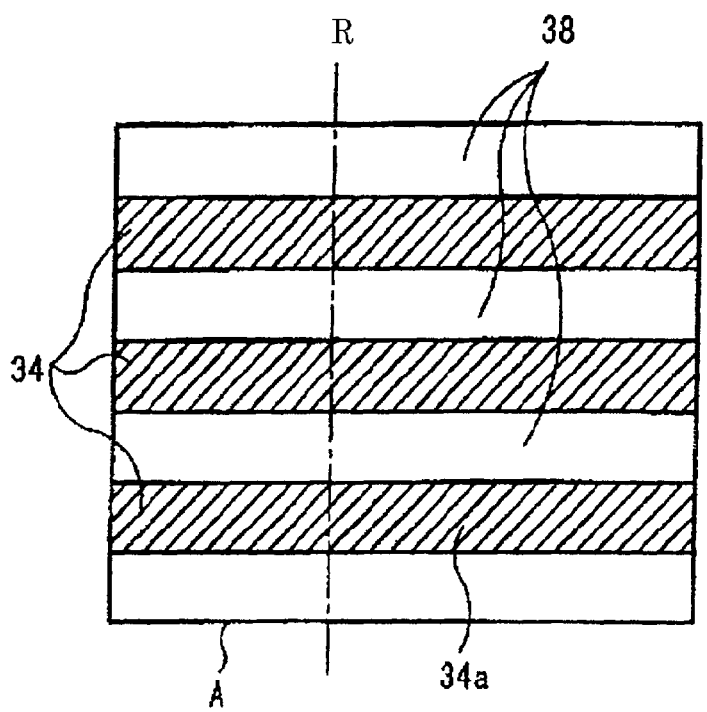
FIG. 14a is a plan view illustrating a reference image and an inspection image in accordance with a conventional defect inspection equipment.
Figure 14C:
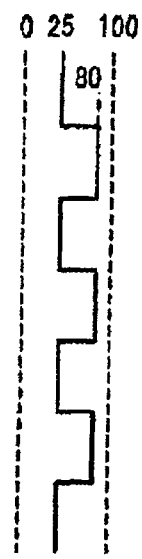
Figure 14B:
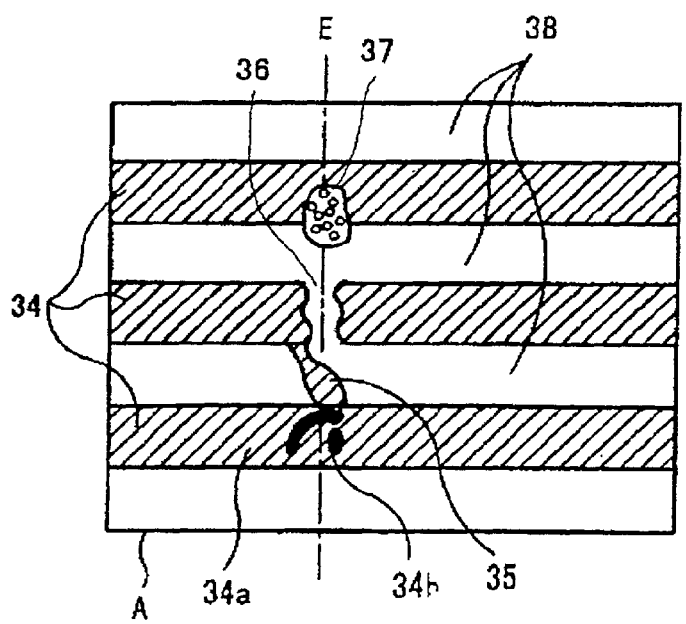
FIG. 14b is a plan view illustrating the reference image and the inspection image in accordance with the conventional defect inspection equipment.
Figure 14D:
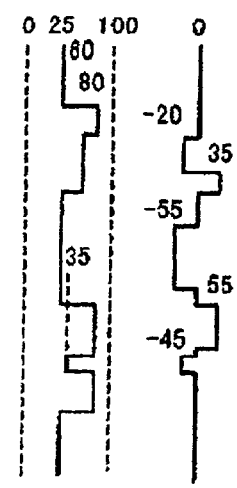
FIG. 14d is graphs showing a pixel signal at a position E in FIG. 14b and a differential signal between the position R in FIG. 14a and the position E in FIG. 14b.

After the operation, as illustrated in FIG. 10, the pixel signal difference between the portion 34a without the roughened portion and the roughened portion 34b is reduced, and the difference from the pixel signal of the oxide film is increased, whereby it is possible to recognize the roughened portion 34b normal and the hiatus 36 of the conductor defective. FIG. 11 is a flow chart explaining a part of the defect inspection method by the above-mentioned procedure according to Embodiment 2, which is interposed in the step of amplifying, positioned between the inspection image data pick-up process 5 and the differential pixel signal operating process 6 in FIG. 2, wherein numerical reference 115 designates a step of judging as follows:

i) when $0 \leq$ current signal $< 90$, new signal value$=2 \times$current signal value$-100$, wherein when new signal value$<0$, new signal value$=0$ ii) when $90 \leq$ current signal value $\leq 100$, new signal value$=$current signal value;

numerical reference 116 designates a step of judging whether or not a pixel signal within an area B is 90 or more;

numerical reference 117 designates a step of adjusting a diaphragm aperture by increasing a light volume;

numerical reference 118 designates a step of judging as follows:

i) when current signal value<100, new signal value=current signal value×current light volume/previous light volume ii) when current signal value=100 new signal value=current signal value; and numerical reference 119 designates "Return".

Although, in this embodiment, the example that the level of the pixel signal is decreased by the numerical process, and is amplified, and thereafter the light volume is again increased is described, c and d may be determined by calculating back to render the roughened portion on the conductor pattern about 90 to omit the step of increasing the light volume again. For example, in a case that the pixel signal value is 50 or more and 100 or less and c=2.036, and d=91.8, the pixel signal value can be expanded to an appropriate width of 10 or more and 90 or less, and it is possible to bring the pixel signal of the roughened portion closer to the saturation pixel signal, whereby the pixel signal difference between the portion 34a without the roughened portion and the roughened portion 34b is reduced to increase the difference from the pixel signal of the oxide film, whereby it is possible to recognize the roughened portion 34b normal and the hiatus 36 of the conductor defective.

Further, although in this embodiment, the example that the level of the pixel signal is decreased by the numerical process and is amplified is described, an electrical pixel signal is subjected to a numerical process, in other words, an electrical offset adjustment and an amplification by an amplifier may be conducted.

The first advantage of the defect inspection method and the defect inspection equipment according to the present invention is that a defect judgment becomes accurate even though the conductor pattern is roughened and therefore the illumination reflectance is decreased. The second advantage of the defect inspection method and the defect inspection equipment according to the present invention is that a defect judgment can be accurate even though the illumination reflectance difference between the roughened portion on the conductive pattern and the oxide film is small.

Obviously, numerous modifications and variations of the present invention are possible in light of the above teachings. It is therefore to be understood that within the scope of the appended claims, the invention may be practiced otherwise than as specifically described herein.

What is claimed is:

1. A defect inspection method comprising the steps of:
    setting an initial value to a light volume of an inspection light illuminating an object to be inspected and picking up an inspection image;
    selecting a normal pattern portion having a roughened surface out of the picked up image and picking up an optical image of the normal pattern portion as a pixel signal in use of an image pick-up device;
    controlling the light volume so that the pixel signal is saturated ;
    picking up a pixel signal of a portion to be inspected and a pixel signal of a reference portion, corresponding to the portion to be inspected, under the controlled light volume; and
    judging an existence of a defect in use of a differential signal between the pixel signal of the portion to be inspected and the pixel signal of the reference portion.

2. The defect inspection method according to claim 1, further comprising:
    a numerically processing step of decreasing a level of the pixel signals, which level is increased by increasing the light volume, and amplifying the pixel signals,
    wherein the numerical processing step is interposed between the steps of picking up the pixel signal and judging the existence of the defect.

3. A defect inspection device comprising:
    a light source illuminating an object to be inspected;
    a diaphragm aperture for adjusting a light volume of an inspection light;
    an image pick-up device introducing the inspection light from the object to be inspected, transforming an optical image formed by the inspection light into electric charges, and picking up as an electric signal;
    an image processing computer for processing the electric signal as a pixel signal of an image;
    an image memory holding a reference image, which is compared with the inspection image;
    a pixel signal pick-up unit selecting and picking up a normal pattern portion having a roughened surface as a pixel signal;
    a pixel signal judging unit for judging whether or not the pixel signal is saturated; and
    a light volume control unit instructing control of the light volume to the diaphragm aperture in accordance with the judgment by the pixel signal judging unit.

4. The defect inspection device according to claim 3, further comprising:
    a pixel signal processing unit for numerically processing to reduce a level of the pixel signal, increased by the increment of the light volume, and to amplify the pixel signal.

5. The defect inspection method according to claim 1, wherein the light volume is controlled so that all of the pixel signal corresponding to the optical image of both the normal pattern portion and the reference portion is saturated.

6. A defect inspection method comprising the steps of:
    controlling a light volume of an inspection light illuminating an object to be inspected so that a pixel signal corresponding to an optical image of a normal pattern portion having a roughened surface is saturated;
    picking up a pixel signal of a portion to be inspected and a pixel signal of a reference pattern, corresponding to the portion to be inspected, under the controlled light volume; and
    judging an existence of a defect based on a difference between values of both pixel signals.

7. The defect inspection method according to claim 6, wherein the light volume is controlled so that all of the pixel signal corresponding to an optical image of a normal conduction pattern portion having a roughened surface is saturated or immediately before saturation.

8. A defect inspection device comprising:
    a light source illuminating an object to be inspected;
    an image processing unit for generating a pixel signal of an image;
    a light volume control unit for controlling the light volume of the light source so that the pixel signal corresponding to an optical image of a normal pattern portion having a roughened surface is saturated;
    a pick up unit for picking up a pixel signal of a portion to be inspected and a pixel signal of a reference pattern, corresponding to the portion to be inspected, under the controlled light volume; and judgment unit for judging an existence of a defect based on a difference between values of both pixel signals.

9. The defect inspection device according to claim 8, wherein the light volume control unit controls the light volume of the inspection light so that all of the pixel signal corresponding to an optical image of a normal conduction pattern portion having a roughened surface is saturated or immediately before saturation.

10. The defect inspection method according to claim 3, wherein the light volume control unit controls the light volume of the inspection light so that all of the pixel signal correspond to an optical image of a normal conductor pattern portion having a roughened surface is saturated or immediately before saturation.

11. The defect inspection method according to claim 6, further comprising:

a numerically processing step of decreasing a level of the pixel signals, which level is increased by increasing the light volume, and amplifying the pixel signals, wherein the numerical processing step is interposed between the picking up of the pixel signal and judging the existence of the defect.

12. The defect inspection method according to claim 8, further comprising:

a pixel signal processing unit for numerically processing to reduce a level of the pixel signal, increased by the increment of the light volume, and to amplify the pixel signal.

* * * * *